(12) United States Patent
O'Grady

(10) Patent No.: US 12,036,133 B2
(45) Date of Patent: *Jul. 16, 2024

(54) METHOD AND SYSTEM FOR PREPARING BONE FOR RECEIVING AN IMPLANT

(71) Applicant: O'Grady Orthopaedics, LLC, Gulf Breeze, FL (US)

(72) Inventor: Christopher Paul O'Grady, Gulf Breeze, FL (US)

(73) Assignee: o'Grady Orthopaedics, LLC, Gulf Breeze, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/943,522

(22) Filed: Sep. 13, 2022

(65) Prior Publication Data

US 2023/0000645 A1    Jan. 5, 2023

Related U.S. Application Data

(63) Continuation of application No. 16/724,899, filed on Dec. 23, 2019, now Pat. No. 11,471,303.
(Continued)

(51) Int. Cl.
*A61B 34/10*    (2016.01)
*A61B 17/16*    (2006.01)
(Continued)

(52) U.S. Cl.
CPC ........ *A61F 2/4609* (2013.01); *A61B 17/1666* (2013.01); *A61B 17/1684* (2013.01); *A61B 34/10* (2016.02); *A61F 2/34* (2013.01); *A61F 2/4081* (2013.01); *A61F 2/4612* (2013.01); *A61B 2017/1602* (2013.01); *A61B 17/1628* (2013.01); *A61B 2034/105* (2016.02);
(Continued)

(58) Field of Classification Search
CPC .............. A61B 34/10; A61B 2034/108; A61B 2034/2055
See application file for complete search history.

(56) References Cited

U.S. PATENT DOCUMENTS

| | | | |
|---|---|---|---|
| 8,160,345 B2 | 4/2012 | Pavlovskaia et al. | |
| 8,403,934 B2 | 3/2013 | Angibaud et al. | |

(Continued)

FOREIGN PATENT DOCUMENTS

WO    2021113227 A1    6/2021

*Primary Examiner* — Nicholas W Woodall
(74) *Attorney, Agent, or Firm* — RMCK Law Group PLC

(57) ABSTRACT

A method of performing arthroplasty of an anatomical joint for receipt of an implant is disclosed. The method includes developing a preoperative plan, designing a patient specific guide based on the preoperative plan, obtaining the patient specific guide, placing the patient specific guide relative to the identified bone, fixing a pair of pins into the bone to establish an Alpha plane and executing the preoperative plan while referencing the Alpha plane. A desired amount of remaining first bone is determined based on a condition of the anatomical joint and a desired orientation of the implant. The patient specific guide includes a pair of bores defined therein and located in positions to accept a complementary pair of pins. The bores are arranged at locations on the patient specific guide to orient the respective pins in a direction optimized for surgeon access to the first bone and to establish the Alpha plane.

18 Claims, 11 Drawing Sheets

Related U.S. Application Data

(60) Provisional application No. 62/787,812, filed on Jan. 3, 2019, provisional application No. 62/879,669, filed on Jul. 29, 2019.

(51) Int. Cl.
    *A61B 34/20*      (2016.01)
    *A61F 2/34*      (2006.01)
    *A61F 2/40*      (2006.01)
    *A61F 2/46*      (2006.01)
    *A61F 2/28*      (2006.01)

(52) U.S. Cl.
    CPC . *A61B 2034/108* (2016.02); *A61B 2034/2055* (2016.02); *A61F 2002/2825* (2013.01); *A61F 2002/2892* (2013.01)

(56) References Cited

U.S. PATENT DOCUMENTS

| | | |
|---|---|---|
| 8,737,700 B2 | 5/2014 | Park et al. |
| 8,974,460 B2 | 3/2015 | Klein et al. |
| 9,168,106 B2 | 10/2015 | Boyer et al. |
| 9,289,253 B2 | 3/2016 | Vanasse et al. |
| 9,517,145 B2 | 12/2016 | Meridew et al. |
| 9,579,106 B2 | 2/2017 | Lo et al. |
| 9,615,840 B2 | 4/2017 | Iannotti et al. |
| 9,795,399 B2 | 10/2017 | Metzger et al. |
| 10,624,764 B2 | 4/2020 | Leone et al. |
| 10,709,508 B2 | 7/2020 | Barnes et al. |
| 10,959,783 B2 | 3/2021 | Gregerson et al. |
| 2007/0066917 A1 | 3/2007 | Hodorek et al. |
| 2009/0018546 A1 | 1/2009 | Daley |
| 2011/0054478 A1 | 3/2011 | Vanasse et al. |
| 2012/0078254 A1* | 3/2012 | Ashby ............... A61B 17/1764 606/87 |
| 2016/0338776 A1* | 11/2016 | Jaramaz ................. G06T 17/10 |

\* cited by examiner

METHOD AND SYSTEM FOR PREPARING BONE FOR RECEIVING AN IMPLANT

CROSS REFERENCE TO RELATED APPLICATIONS

This application is a continuation of U.S. patent application Ser. No. 16/724,899 filed Dec. 23, 2019, which claims priority to U.S. Provisional Application No. 62/787,812 filed on Jan. 3, 2019 and 62/879,669 filed on Jul. 29, 2019. The disclosures of the above applications are incorporated herein by reference.

FIELD

The present disclosure relates generally to a method and system for preparing bone for receiving an implant.

BACKGROUND

Various anatomical joints may undergo degenerative changes. In some instances it may be desirable to replace a natural joint with a prosthetic joint. More common joints including, but not limited to the shoulder, knee, hip can be successfully replaced in an orthopedic surgical procedure. Sometimes the difficulty in adequately exposing the bone and tissue creates problems and errors in accurately implementing a desired surgical procedure. Moreover, it would be desirable to provide a method and system that accurately prepares the desired area for receipt of a desired implant while minimizing errors that may result from a surgeons tools guided only by hand and direct intraoperative vision.

The background description provided herein is for the purpose of generally presenting the context of the disclosure. Work of the presently-named inventor, to the extent it is described in this background section, as well as aspects of the description that may not otherwise qualify as prior art at the time of filing, are neither expressly nor impliedly admitted as prior art against the present disclosure.

SUMMARY

A method of performing arthroplasty of an anatomical joint for receipt of an implant is disclosed. The method includes developing a preoperative plan, designing a patient specific guide based on the preoperative plan, obtaining the patient specific guide, placing the patient specific guide relative to the identified bone, fixing a pair of pins into the bone to establish an Alpha plane and executing the preoperative plan while referencing the Alpha plane. Developing the preoperative plan includes establishing a desired amount of remaining first bone based on a condition of the anatomical joint and a desired orientation of the implant. The patient specific guide includes a pair of bores defined therein and located in positions to accept a complementary pair of rigid pins. The bores are arranged at locations on the patient specific guide to orient the respective pins in a direction optimized for surgeon access to the first bone and to establish the Alpha plane. The preoperative plan includes known locations of the first bone relative to the Alpha plane.

According to additional features, executing the preoperative plan includes coupling optical arrays to the pair of pins at a known distance from the first bone. A position of the cutting tool relative to the Alpha plane is correlated using the optical arrays. Desired portions of the first bone are removed with the cutting tool while referencing exclusively the Alpha plane to determine a position of the cutting tool based on the preoperative plan. In another arrangement, executing the preoperative plan includes connecting a cutting tool relative to at least one of the first and second pins. The cutting tool is moved relative to at least one of the first and second pins along the Alpha plane. Desired portions of the first bone are removed with the cutting tool while referencing exclusively the Alpha plane to determine a position of the cutting tool based on the preoperative plan.

In other features, removing desired portions of the first bone includes resecting the first bone in a pattern to match a geometry of an implant. The cutting tool can be motorized. Connecting the cutting tool can include clamping a portion of the cutting tool to at least one pin for translation of the cutting tool along the pin. Removing desired first portions of bone can include translating the cutting tool along the Alpha plane. First portions of the first bone can be reamed with the cutting tool at a first cutting angle based on the preoperative plan. An arm on the cutting tool can be articulated to establish a second cutting angle, distinct from the first cutting angle. The cutting tool can be further translated along the Alpha plane. Second portions of the first bone can be reamed with the cutting tool at a second cutting angle based on the preoperative plan.

According to additional features, the cutting tool can communicate wirelessly with a computer having the preoperative plan. The computer can comprise one of a workstation, desktop, laptop, tablet, mobile phone, wearable accessory or garment. The cutting tool can comprise a reamer. The cutting tool can further comprise an end-cutting milling device. The first bone can be a glenoid and the implant can be a glenoid implant. The first bone can alternatively be a femur and the implant can be a femoral implant. The first bone can alternatively be a tibia and the implant can be a tibial implant. The first bone can alternatively be an acetabulum and the implant can be an acetabular implant.

A system for performing arthroplasty of an anatomical joint for receipt of an implant according to the present disclosure includes a patient specific guide, a computer and a cutting tool. The patient specific guide has a pair of bores defined therein and located in positions to accept a complementary pair of pins. The bores are arranged at locations on the patient specific guide to orient the respective pins in a direction optimized for surgeon access to the first bone and to establish an Alpha plane. The computer develops a preoperative plan that includes a desired bone cutting depth of a first bone and a desired amount of remaining first bone based on a condition of the anatomical joint. The preoperative plan includes known locations of the first bone relative to the Alpha plane. The computer designs the patient specific guide. The cutting tool executes the preoperative plan while referencing the Alpha plane.

In additional features, the system further includes a pair of optical arrays configured to be coupled to the respective pair of pins. A position of the cutting tool is correlated to the Alpha plane using the pair of optical arrays such that desired portions of the first bone are removed with the cutting tool while referencing the Alpha plane based on the preoperative plan. The tool can comprise a robotic cutting tool having a fixing portion, a cutting portion and an arm. The fixing portion can locate relative to at least one pin. The cutting portion can be configured to cut the first bone. The arm can be disposed between the fixing portion and the cutting portion. The arm can articulate to change an angle of the cutting portion relative to the Alpha plane to cut the desired bone according to the preoperative plan. The cutting portion can include one of a reamer and an end-cutting milling device. At least one of the first and second pins can comprise a threaded portion. The fixing portion can locate relative to the threaded portion.

BRIEF DESCRIPTION OF THE DRAWINGS

The present disclosure will become more fully understood from the detailed description and the accompanying drawings, wherein.

DETAILED DESCRIPTION

The ultimate goal in placing orthopedic prostheses (joint replacements, etc.) is to insert them in a very precise orientation in order to best restore normal anatomy and to preserve bone. Proper orientation will maximize the longevity of the implant and provide the best outcome for the patient. There are many preoperative planning tools available to create a patient-specific operative plan. These plans typically work off a 3-D model obtained from a CT scan or MRI of the body part targeted for surgery. The most challenging problem lies in the execution of these plans, especially in the hands of low volume surgeons. The present disclosure provides a novel method to establish a static reference plane, hereinafter "Alpha plane" using two parallel pins placed through a patient specific guide. The patient specific guide is designed based on a preoperative plan. Once the pins are located into bone at positions predetermined by the guide, the guide is removed. Surgical tools, including robotic assisted tools, reference this static Alpha plane during the procedure to precisely execute the preoperative plan. The geometry of each patient specific guide is designed and created specific to the patient's anatomy and determined bone preparation. The geometry is also specifically designed to direct placement of the pins (that establish the Alpha plane) in a location out of the way of the surgeons working area optimized for surgeon access and visibility to carry out bone resection. As will become appreciated from the following discussion, the system and methods disclosed herein provide a much simpler yet accurate way for accomplishing arthroplasty.

The present disclosure pertains to a bone preparation system and related method utilizing a patient specific guide configured to match a section of bone. The instant application contemplates surgical procedures involving the shoulder, knee and hip discussed in sequence below. Those skilled in the art will appreciate that the instant application may also be adaptable to other anatomical joints.

Figure 1:
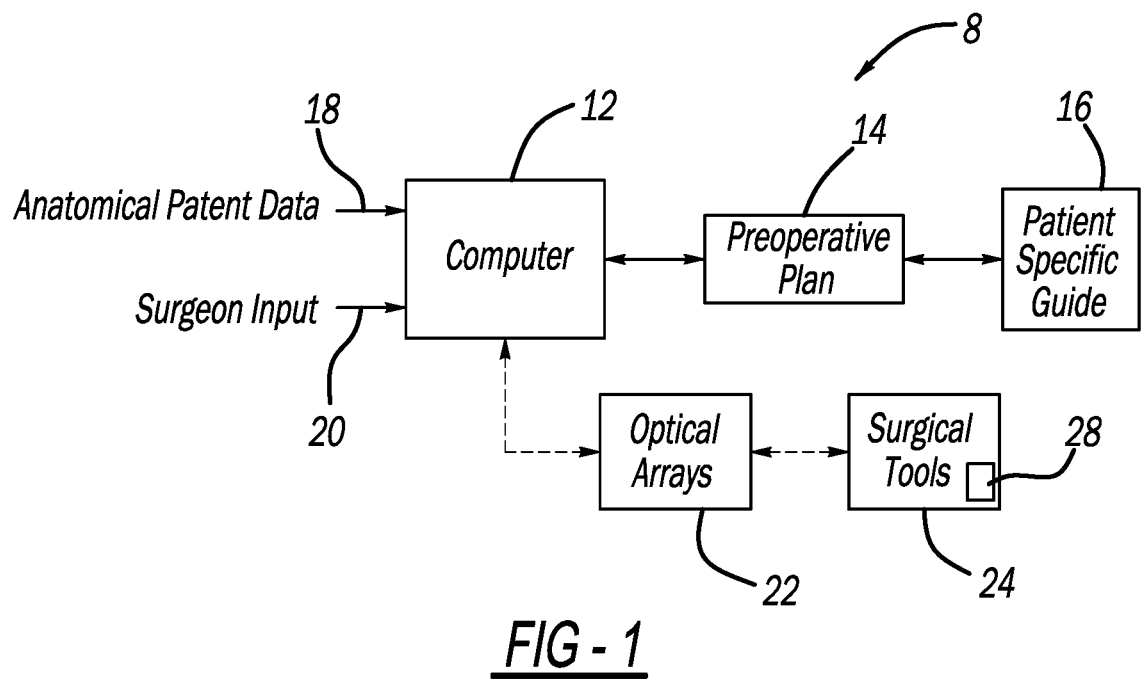
FIG. 1 is a schematic view of a system for performing arthroplasty of an anatomical joint for receipt of an implant.

With initial reference to FIG. 1, a system for performing arthroplasty of an anatomical joint for receipt of an implant is shown and generally identified at reference numeral 8. The system 8 generally comprises a module, processor or computer 12, a preoperative plan 14 and a patient specific guide 16. The computer 12 uses code to develop a preoperative plan that includes a desired cutting depth of a first bone based on anatomical patient data 18 and surgeon input 20. Anatomical patient data 18 can be obtained by any suitable method such as by a CT scan, MRI or other imagery of the anatomical joint. As will be described herein, the system 8 can further include one or more optical arrays 22 and surgical instruments or tools 24 that communicate with the computer 12 to identify a location of the tool 24 relative to the preoperative plan 14.

The instant teachings requires minimal instrumentation and steps to establish known positions of the patients' anatomy relative to the surgical bone preparation needed to be carried out. As explained herein, a reference plane, hereinafter "Alpha plane" 40 is established by the patient specific guide 16 that directs placement of two pins 30, 32 into the appropriate bone along the reference plane 40. The two rigid pins 30, 32 can be referenced directly or indirectly during future surgical bone preparation by the surgical cutting tools 24 such as a robotic tool or hand held tool. A robotic tool can directly reference one or both pins 30, 32. Additionally or alternatively, the optical arrays 22 can be coupled (clipped or otherwise affixed) to the two pins 30, 32. The location of a hand held tool 24 can then be determined based on its position relative to the optical arrays 22 fixed to the pins 30, 32. In either scenario, the location of the tools 24 is known relative to the Alpha plane 40.

As the location of the pins 30, 32 (and Alpha plane 40) is known and determined by the preoperative plan 14, no subsequent surface mapping is required. Further, no additional pins are needed to be inserted into the bone. A location of the tool 24 will be known based on its location relative to the Alpha plane 40 using the optical arrays 22. As such, the location of the tool 24 can be correlated to the patient's anatomy using the preoperative plan 14 and known locations of the Alpha plane 40. Explained differently, the two pins 30, 32 define an invisible static plane (Alpha plane 40) across the bone. The computer 12 will treat the two pins 30, 32 as a reference plane 40 that matches up exactly with the preoperative plan 14. The surgical procedure can then work off of the Alpha plane 40. In this regard, the location of areas of bone categorized by the preoperative plan 14 for resection are known relative to the Alpha plane 40. Similarly, locations of surgical tools 24 will be known relative to the Alpha plane 40. As such, surgical bone preparation can be carried out with certainty and minimal preparation.

In one example, a tool 24 having a cutting burr can be used to cut away areas of bone identified by the preoperative plan for resection. The tool 24 can include an optical array 28 that communicates to the computer 12 the position of the burr relative to the Alpha plane. As the preoperative plan includes anatomical information of the patients' anatomy relative to the Alpha plane, the position of the tool 24 is known relative to the patients' anatomy. Because the location of the tool 24 is known, the preoperative plan 14 will only allow the cutting burr to travel and cut into locations of the patients' anatomy identified for resection. Some instruments may allow for the cutting burr to retract to preclude unwanted cutting. Other tools may provide haptic feedback or other warnings to convey a position of the tool 24 to a surgeon.

With continued reference to FIG. 1 and additional reference to FIGS. 2-7C, a method for performing shoulder arthroplasty according to one example of the present disclosure will be described. A preoperative plan is developed based on anatomical patient data and surgeon input. A patient specific guide 16A is designed by the preoperative plan. The patient specific guide 16A can then be manufactured based on the design. After obtaining standard surgical exposure of a glenoid 10, the patient specific glenoid guide 16A (FIGS. 7A-7C) will be placed engaging the base of the coracoid as well as the anterior glenoid 10. The patient specific guide 16A defines two cannulations or parallel bores 50, 52 that receive and will allow the placement of two parallel pins 30, 32 which will enter the anterior glenoid 10 at the base of the coracoid. As mentioned, the pins 30 and 32 are used in one example to define the Alpha plane 40 (FIG. 2) that will subsequently serve as a reference to the patients' anatomy. In a second example, the pins 30 and 32 can serve as a physical connection point where tools 24 can be coupled thereto for performing bone preparation to execute the patient specific plan. Both examples are discussed below.

By using the pins 30 and 32 (and ultimately the Alpha plane 40) as a reference, many laborious steps carried out in prior art examples can be avoided. Explained further, in some prior art procedures, registering a patients' anatomy requires extensive planning and steps such as locating multiple drill pins, and an elaborate sequence of surface mapping using optical arrays and a sensor probe. In this regard, prior art methods require drilling into bone (glenoid, femur, etc.) and positioning multiple optical arrays as part of a registration process. In one prior art process, pins are drilled into bone to establish an anatomical axis and the optical arrays are coupled to the pins. A probe is used to touch the surface of the identified bone in multiple locations to create a three-dimensional model of the bone on a computer.

By way of example, during a conventional knee replacement surgery, a surgeon typically drills two pins into the femur and couples a femoral optical array to the pins. Similarly, a surgeon drills two additional pins into the tibia and fixes a tibial array to those pins. Next, the surgeon uses a sensor probe to carry out a registration process. During the registration process the surgeon touches the distal femur and proximal tibia with the sensor probe. In some implementations the computer will instruct the surgeon to touch specific landmarks. Furthermore, the tip of the sensor probe can be rubbed against the distal femur and proximal tibia to map the positions to the computer. The computer collects real time data points provided by the sensor probe. The locations that are read by the computer are used to build a three-dimensional model. This prior art method to build a three-dimensional model using elaborate registering and mapping is time consuming. Moreover, the joint is exposed for long periods of time while obtaining the data with the sensor probe.

Figure 2:
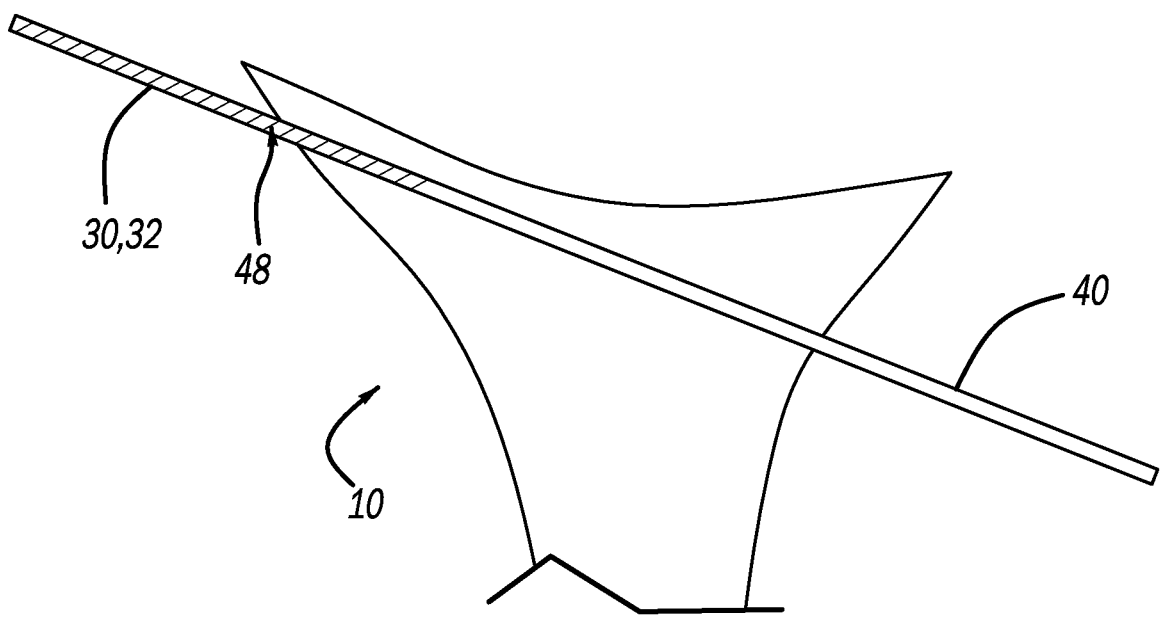
FIG. 2 is an axial view of a glenoid showing a pair of pins inserted therein during establishment of the Alpha plane.
Figure 3:
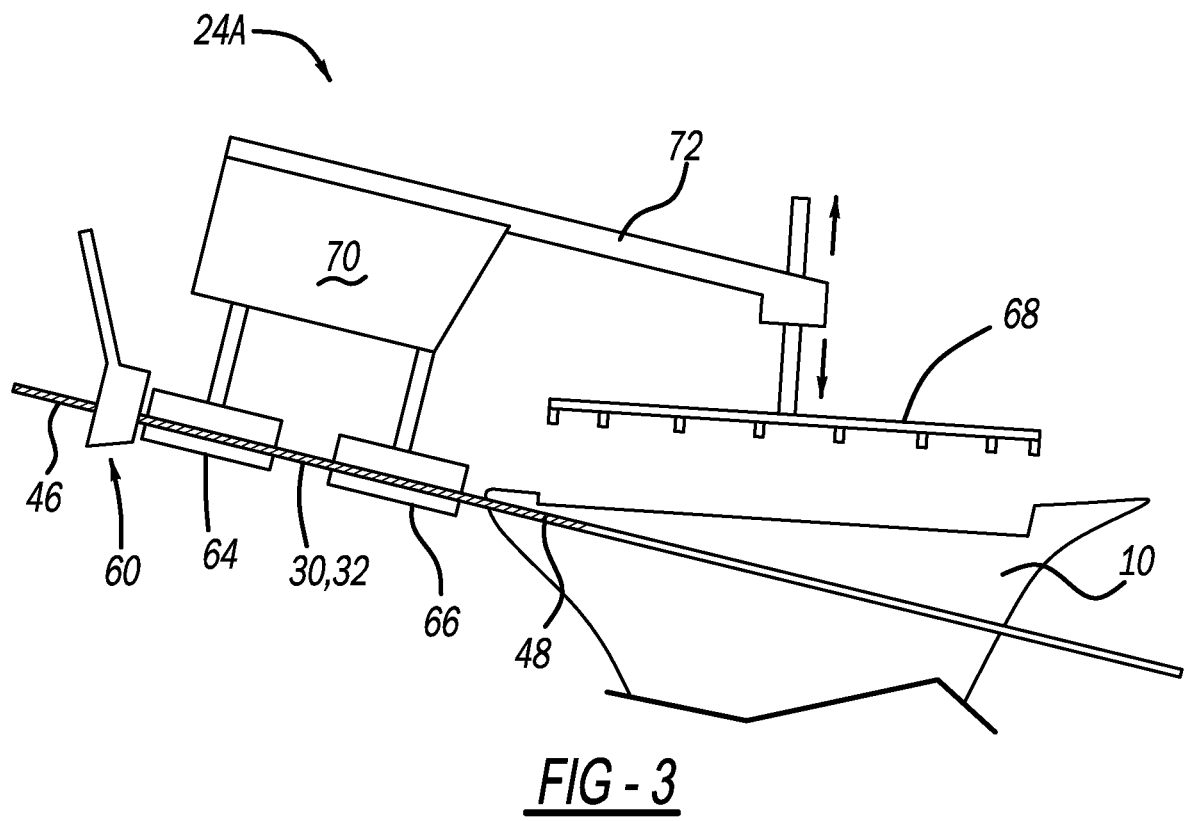
FIG. 3 is an axial depiction of a motorized remotely controlled cutting tool constructed in accordance to one example of the present disclosure.
Figures 6, 7A:
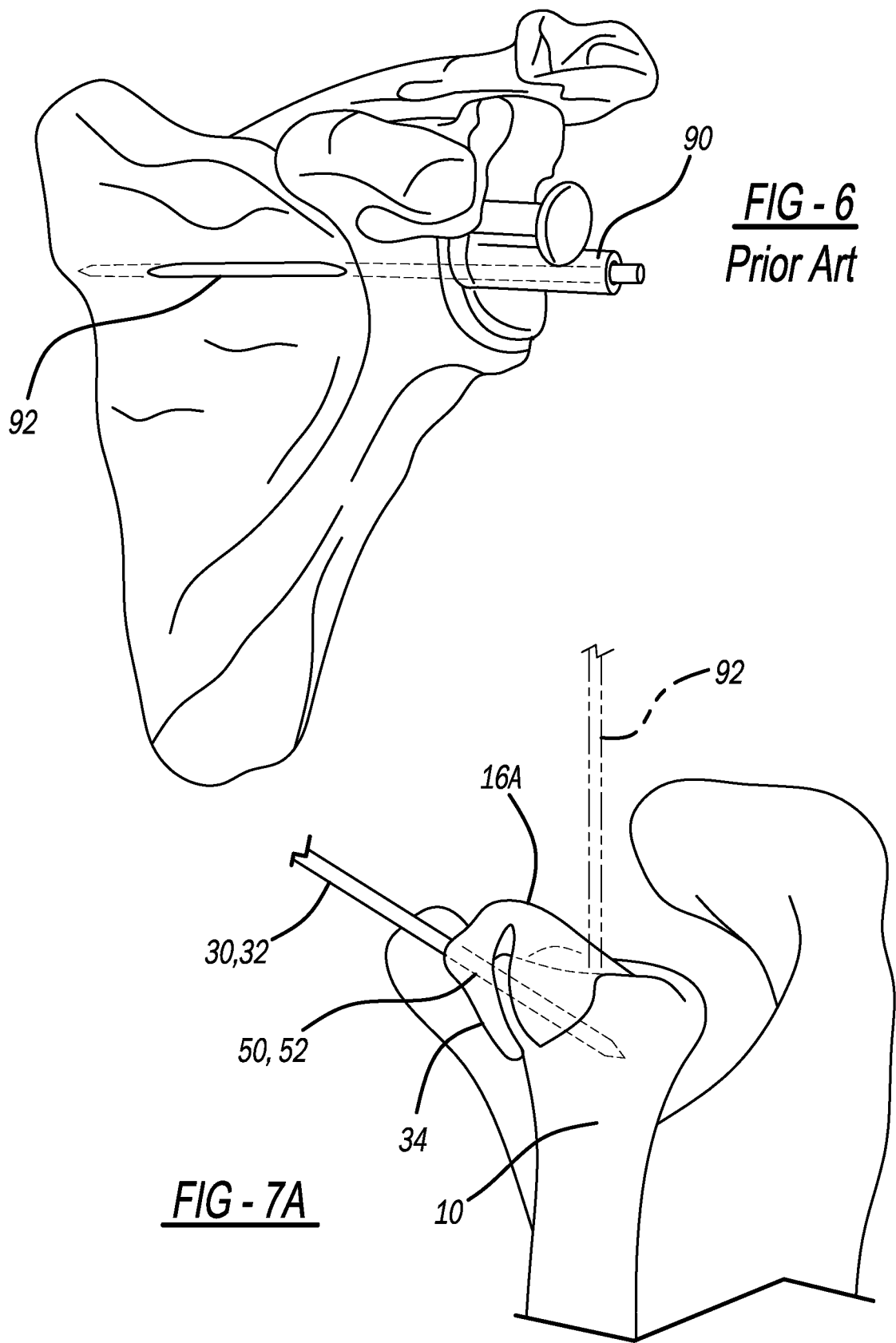
FIG. 6 is an anterior/lateral view of a glenoid showing a patient specific guide that identifies a neutral axis according to one prior art example.
FIG. 7A is an axillary view of a patient specific glenoid guide constructed in accordance to one example of the present disclosure and located relative to a glenoid and further shown with a pair of pins directed into the glenoid by the patient specific glenoid guide at locations determined by a preoperative plan.
Figure 7B:
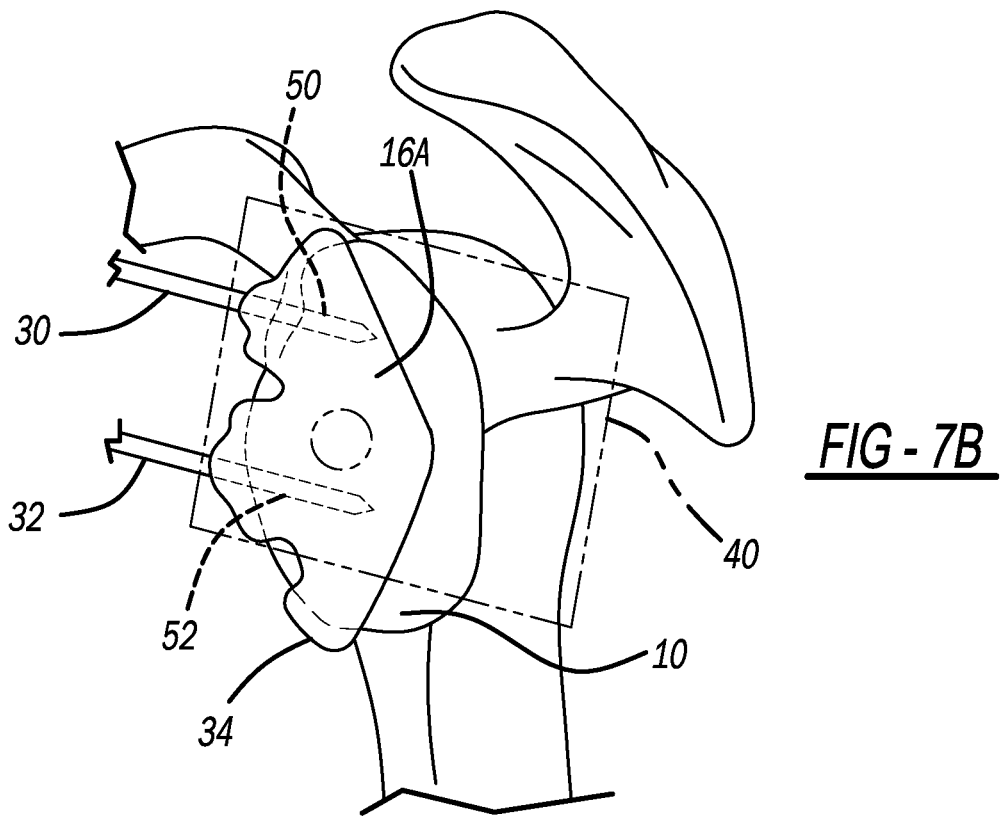
FIG. 7B is an anterior/posterior view of the patient specific glenoid guide and glenoid of FIG. 7A.
Figure 7C:
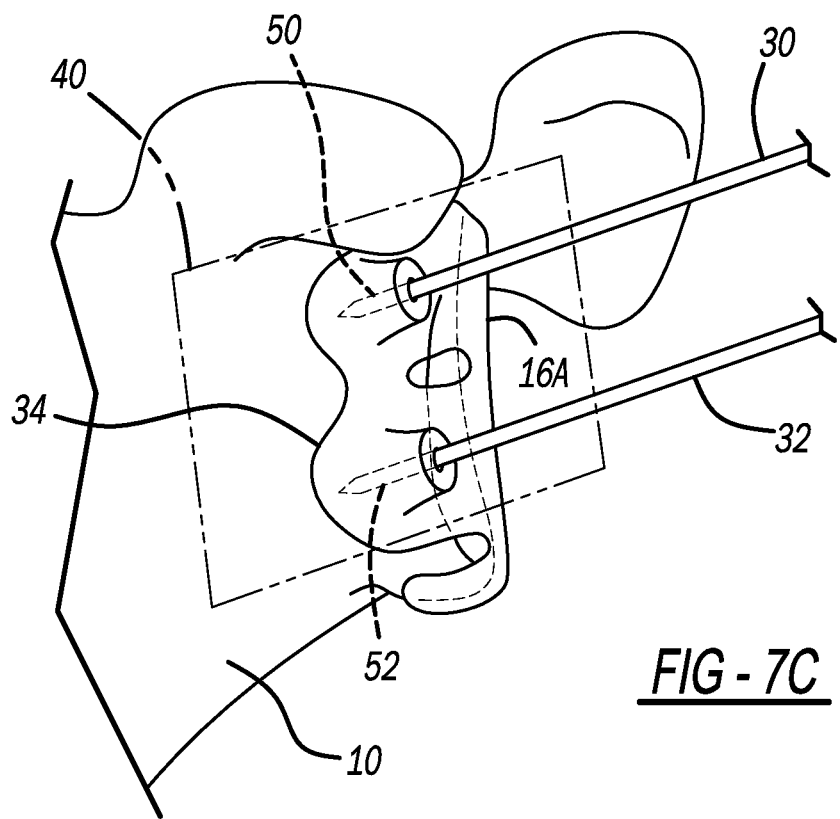
FIG. 7C is a lateral view of the patient specific glenoid guide and glenoid of FIG. 7A.

With particular reference to FIGS. 7A-7C, the patient specific glenoid guide 16A will be further described. It will be appreciated that the geometry of the patient specific glenoid guide 16A is merely exemplary and that the glenoid guide 16A may take other shapes. The glenoid guide 16A can further include a footing 34 that helps position the guide 16A at the desired location on the glenoid 10. One of the pins 30, 32 is located more distally to the other pin. The pins 30, 32 are parallel to each other in the anterior glenoid vault. The purpose of the first pin 30 is to utilize the dense bone at the base of the coracoid. The coracoid base is a readily identifiable landmark during glenoid exposure. This stands true even in cases of severe glenoid deformity or coracoid transfers. This will allow for the two pins 30, 32 to be rigidly placed establishing the Alpha plane 40. The Alpha plane 40 will establish a reference plane for future procedures. In one example, a location of handheld surgical tools (such as a cutting tool 24) is known based on its location relative to the Alpha plane 40. In other examples, the Alpha plane 40 can serve as a working plane for a motorized cutting tool 44 (FIG. 3). After the pins 30, 32 have been advanced into the glenoid 10 (FIGS. 7A-7C), the patient specific glenoid guide 16A will be removed leaving the pins 30, 32 in the bone 10 (FIG. 2).

Figure 4:
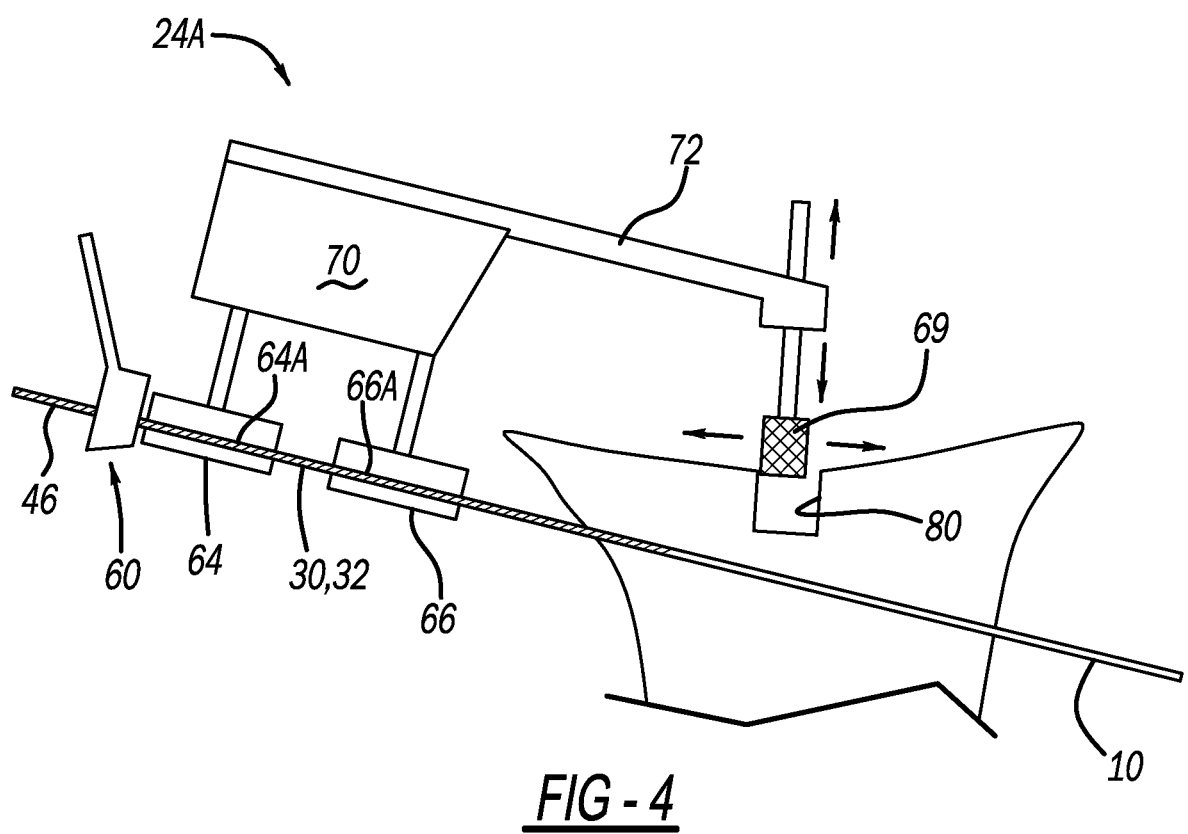
FIG. 4 is an axial depiction of the motorized cutting tool of FIG. 3 incorporating a milling bit according to one example of the present disclosure.

With particular reference now to FIGS. 3 and 4, additional features of the system 8 will be described. The pins 30, 32 can have a threaded portion 46 and have laser etch marks 48 such as every 5*mm* in order to determined depth into the glenoid vault. The depth can be pre-calculated by the preoperative plan 14. A cutting tool 24A includes a locking mechanism 60. The threaded portions 46, 48 can facilitate coupling of the locking mechanism 60 on the motorized cutting tool 24A. The motorized cutting tool 24A can have feet 64, 66 that define two cannulated slots 64A, 66A that receive the pins 30, 32 extending from the glenoid 10. The two cannulated slots 64A, 66A can define a distance apart that is satisfactory and uniform for use in all surgeries. In one exemplary method, the slots 64A, 66A defined in the feet 64 and 66 can be aligned for receipt of the pins 30, 32. The feet 64 and 66 can then be traversed along the pins 30, 32 until engaging the glenoid 10 such as at the base of the coracoid. The locking mechanism 60 can then be locked in place precluding the feet 64 and 66 from further movement. This will now be in place to carry out the preoperative reaming plan.

The motorized cutting tool 24A can include a reamer 68 (FIG. 3). The motorized cutting tool 24A can include a main body 70 that supports the feet 64 and 66. An articulating arm 72 extends from the main body 70 to the reamer 68. The articulating arm 72 can articulate to change an angle of the reamer 68 relative to the Alpha plane 40 while carrying out the preoperative plan 14. The reamer 68 can be provided in many shapes and sizes distinct from what is shown in FIG. 3. In one example the reamer 68 is a standard circular reamer with aggressive cutting teeth allowing for an aggressive but precise cuts. For anatomic glenoids with no defect it will simply ream at a predetermined angle and approach the Alpha plane 40 defined by the pins 30, 32 and stop based on the pre-operative plan. If there is an augment needed posteriorly the tool 24A can articulate for a second pass and then ream again at the predetermined angle matching the augment of a wedged anatomic or reverse base plate configuration.

In another configuration, the motorized cutting tool 24A can comprise a milling device 69 (FIG. 4) that will be inserted into the glenoid 10 in the same way. The milling device 69 will also use the Alpha plane 40 defined by the pins 30, 32 as a reference to determine a position of the milling device 69 relative to the patients' anatomy to mill out the exact configuration to prepare a bone cavity 80 into the glenoid 10. The bone cavity 80 can match the backside of a desired implant consistent the preoperative plan 14. It is contemplated that the bone cavity 80 can be prepared to accommodate a center keel 82 of an implant 84 (FIG. 5B). In other examples, bone cavities can alternatively or additionally be prepared to accommodate peripheral pegs on the implant 84, posterior augments or other geometries related to the implant.

The motorized cutting tool 24A will network either directly or wirelessly to the computer 12. The computer 12 will have the geometry of the patient specific guide 16 saved, either on a local hard drive or on an accessible network, and will mirror the surgeon's preoperative plan 14. Once the desired cuts have been performed, the motorized cutting tool 24A can be removed along with the pins 30, 32. The implantation of a glenoid implant now proceeds through standard techniques.

Traditional methods may utilize a preoperative plan based on 3D, CT or MRI. The execution of the plan depends on precise placement of a pin in the neutral axis followed by the use of cannulated reamers. There can be challenges in placing that pin because of difficulty in obtaining adequate surgical exposure. Even in cases of accurate pin placement there can be inaccuracies in both depth and rotation of reaming.

The system and method according to the present teachings is different in that it establishes and utilizes the Alpha plane 40 as an intraoperative reference. In some prior art examples such as the prior art patient specific guide 90 (FIG. 6), the guide assists in establishing a neutral axis along a pin 92. Once the location of the pin 92 has been established, the patient specific guide 90 can be removed. The pin 92 can then be referenced by various cannulated reamers to cut away the bone to create the cavity that matches a profile of the implant. In many instances, it can be difficult to provide adequate spacing from surrounding anatomy (humeral head, etc.) for such reamers to approach the bone along the pin 92 (neutral axis) making the process challenging in the prior art arrangement of FIG. 6. Many times the humeral head needs to be forced out of the way so as not to interfere with instrument approaches along the pin 92. As explained, while the neutral axis can assist a surgeon in establishing a desired orientation of the implant, the guide 90 and pin 92 can obstruct a surgeon's preferred approach to the glenoid during resection of bone. The instant methods allow for improved accessibility for the surgeon to perform the necessary cuts on the glenoid.

The system and method of the instant application contemplates the use of the pins 30 and 32 in one example for registration with optical arrays. In another example, the pins 30 and 32 can be used for direct or indirect contact by a motorized (robotic) cutting tool. The system and method also differs from prior art examples that reference the neutral axis in that it uses the motorized cutting tool 24A to resect bone in a precise manner, not as measured by the amount resected, but measured by the amount of bone that will remain as it relates to the Alpha plane 40. Traditional preoperative planning is the same in that a 3D CT is obtained in order to define the morphology and the abnormalities in the glenoid. Current technology will allow for the design of a guide that mates to the patient's glenoid and its irregularities. Traditionally the goal has been to attach a drill guide allowing for the placement of a pin down the neutral axis. The instant disclosure utilizes an easy and identifiable landmark for all surgeons, the base of the coracoid. Not only is this identifiable but it is an excellent source of bone for the primary pin. The second difference is to use two pins 30, 32, not one, and to align the pins 30, 32 not along a neutral axis of the scapula, but use them to define the Alpha plane 40. In this regard, instead of one pin along the neutral axis, there will be two pins 30, 32 defining a plane posterior to the glenoid. This Alpha plane 40 will be entering the surgical field at an oblique angle correlating to the angle of the original incision at the deltopectoral interval.

The pins 30, 32 will allow for the entry of the motorized cutting tool 24A into a space large enough for preparation. It is anticipated that the space required for the motorized cutting tool 24A will be less than currently needed for traditional methods and therefore require less traumatic dissection and less difficulty obtaining glenoid exposure. The angle of the pins 30, 32, and therefore the angle at which the motorized cutting tool 24A will enter will alleviate some of the struggles of having to bring all reaming instruments in along a neutral axis. In traditional exposure there are struggles with trying to work around the humeral head. The method according to the present teachings will allow for entry of the motorized cutting tool 24A into the glenohumeral joint at an angle that approaches that of the deltopectoral approach and will have less obstruction in difficult exposure cases. As can be appreciated, all the bone work occurs on the surface of the glenoid. The instant teachings provide a method that places the pins 30, 32 posterior and medial to the glenoid in a position that is out of the way of a surgeons approach to the glenoid surface. For comparison purposes, the prior art pin 92 defined along the neutral axis is shown in broken line in FIG. 7A along with the pins 30, 32 of the instant teachings. As shown, the pins 30, 32 are in a more advantageous orientation compared to the pin 92 that will allow for improved surgeon accessibility.

With the Alpha plane 40 defined by the pins 30, 32, the motorized cutting tool 24A will be locked in place and will be able to execute the plan by referencing the Alpha plane 40 defined by those two pins 30, 32. The motorized cutting tool 24A can track along at least one of the pins 30, 32 thereby maintaining reference to the Alpha plane 40. In some examples, the surgeon can manually translate the motorized cutting tool 24A along at least one of the pins 30, 32 by hand. In other examples the motorized cutting tool 24A can be powered along at least one of the pins 30, 32 by an internal or external propulsion mechanism such as a motor. In still other examples, the motorized cutting tool 24A can move along at least one of the pins 30, 32 by combinations of manual (surgeon assisted) and automatic (motor powered) movements. This method will not only achieve the goal of planning for component optimization preoperatively, but it allows for precise execution of the preoperative plan 14 by the motorized cutting tool 24A. It will also be able to resect bone in any configuration, fitting the backside of any glenoid component, such as glenoid component 84, FIG. 5B. The motorized cutting tool 24A can also take the form of a powered multi-plane reamer, a multi-plane saw, or a milling device. After initial cuts are made to match the back side of the prosthesis to be implanted, the slots or peg holes needed to match those on each prosthesis can be drilled by the milling bit 69 or by a drill press type tool exchanged onto the same track defined by the pins 30, 32.

Figure 5A:
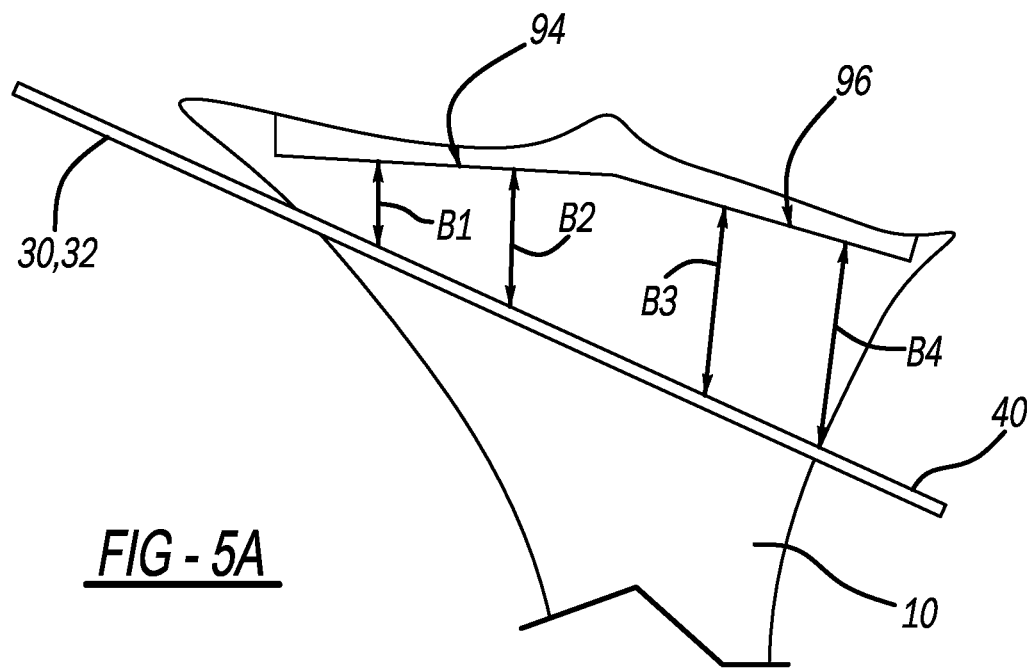
FIG. 5A is an axial view of the glenoid of FIG. 1 illustrating first and second cuts performed by the cutting tool of FIG. 3 while referencing the Alpha plane according to one example of the present disclosure.
Figure 5B:
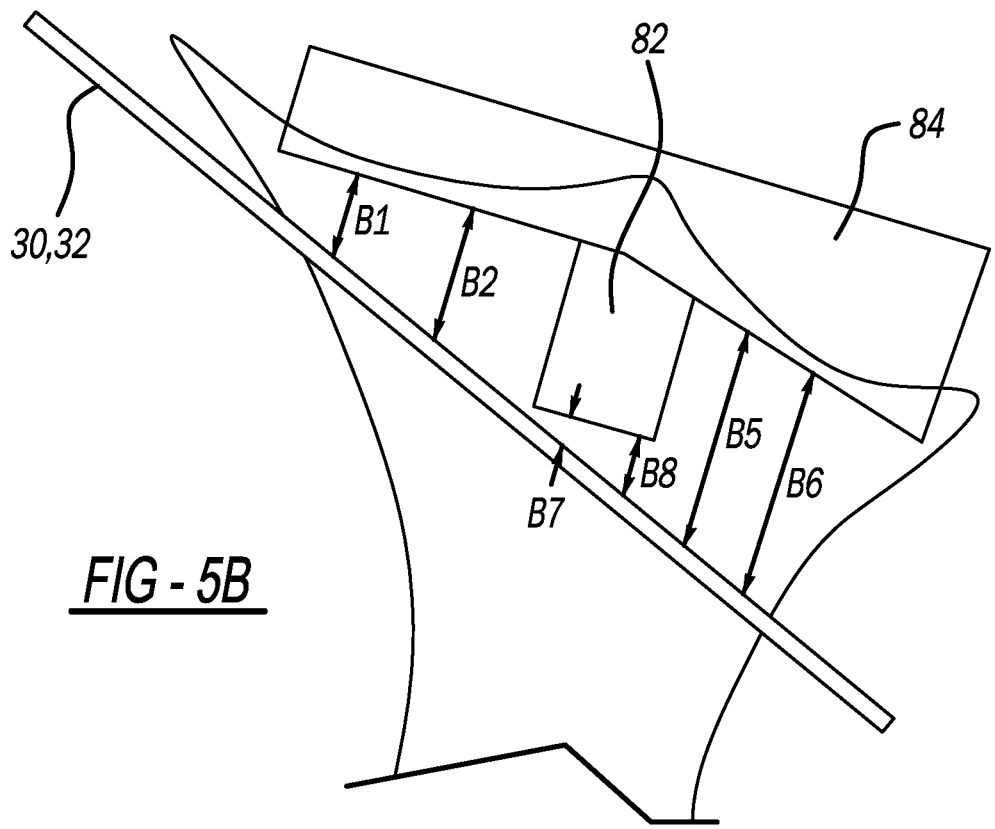
FIG. 5B is an axial view of the glenoid of FIG. 5A and showing an exemplary glenoid component to be implanted at the surgical site prepared by the cutting tools of FIGS. 3 and 4.

With particular reference to FIGS. 5A and 5B, additional features will be described. The importance of the Alpha plane 40 is that software executed by a processor in the computer 12 can determine precise locations identified for bone resections measured from the Alpha plane 40. The preoperative plan 14 will dictate the amount of bone that will be removed and will remain in the glenoid vault. Any tissue, including bone, cartilage, etc., between the reaming/milling device and that calculated to remain as measured off the Alpha plane 40, will be resected via reaming/milling. The shape of the backside of the desired implant 84 (including extensions such as a keel 82) will be exactly mirrored by that remaining in the glenoid vault. It will also be in the exact orientation and position dictated by the preoperative plan 14.

An algorithm contained in the software and used by the computer 12 will measure the distance between the Alpha plane 40 medially and the desired amount of remaining bone as measured between the Alpha plane 40 and a desired resection depth "B1, B2, B3, B4, B5, B6, B7, B8 etc." to accept the implant 84. This distance, BETA, can be measured from the anterior to posterior in an infinite number of measurements in order to improve accuracy. This measurement will also be calculated on every axial CT or MRI cut. The compilation of these measurements will define a three-dimensional shape which will correlate exactly to the backside of the implant 84. While a particular implant 84 is shown in FIG. 5B it is appreciated that the present teaching can be used to prepare bone for receipt of any implant such as, but not limited to anatomic, reverse, or augmented components.

By way of further description, the bone preparation tool 24A of the present disclosure will replace tools that are now 100% manual and depend on the surgical technique of the surgeon and the visual ability to determine depth and rotation. Even in experienced hands this can lead to errors. The motorized cutting tool 24A will be locked in place and will execute the bone reaming based on predetermined measurements. These measurements will be pre-determined by the templating software and will be specific to each patient. The motorized cutting tool 24A will be able to interface with the computer 12 such as in the operating room that executes the software program containing the preoperative plan 14 to the patient having the specifications for the appropriate implant in the correct orientation. In some examples the motorized cutting tool 24A can interface wirelessly such as by Bluetooth or Wi-Fi. It is further contemplated that the preoperative plan 14 can be developed and/or communicated by a computer 12 comprising at least one of a workstation, desktop, laptop, tablet, mobile phone, wearable accessory or garment.

The motorized cutting tool 24A can have a circular reamer which is the traditional method and is basically an aggressive rasp. It smooths the bone to a shape that will accept the implant. The implant shape is usually flat or slightly curved depending on its design. The reamer 68 can also articulate (by way of arm 72, FIG. 3) therefore having the ability to ream in two different angles. This will create two flat surfaces 94, 96 (FIG. 5B) that are at different angles and will be able to accept augmented glenoids that have these irregular shapes.

In another example, the cutting tool can include the bone milling device 69, FIG. 4. The bone milling device 69 can utilizes an end-cutting milling device that resects bone into the same configurations as described above. The bone milling device 69 will work in three dimensions and replicate the preoperative plan 14 in three-dimensions. The tool 24A will pre-contour any shape into the bone 10 that is programmed and will match that of each individual glenoid component as determined by the preoperative planning software executed by the computer 12. The bone mill 69 will have the ability to contour flat surfaces, and it will also be able to drill narrow cylinders matching the shape of the peripheral pegs, central keels, and any other designs of different glenoid components.

The design of the bone milling device 69 will be such that the working end will be narrow, and the internal mechanisms and technology that is used to interface with the software will reside in the handle. This will allow for a low-profile device entering in the direction of the deltopectoral surgical approach. It will minimize the need for excessive pressure on the humeral head during glenoid exposure. Glenoid exposure is the most difficult part of shoulder replacement surgery and so the tool 24A will dramatically reduce the struggle in obtaining this exposure and executing the preoperative plan 14 for each patient.

As mentioned above, in other examples, the optical arrays 22 can be fixed to the pins 30, 32 at known locations a predetermined distance from the first bone. The optical arrays can then register their position in space to a computer 22 (or robot) where the exact positions of the pins 30, 32 is known. Once the exact position of the pins 30 and 32 has been established, a surgeon can then proceed with bone preparation while referencing the known locations of the pins 30, 32 relative to the anatomy in space.

Figure 8A:
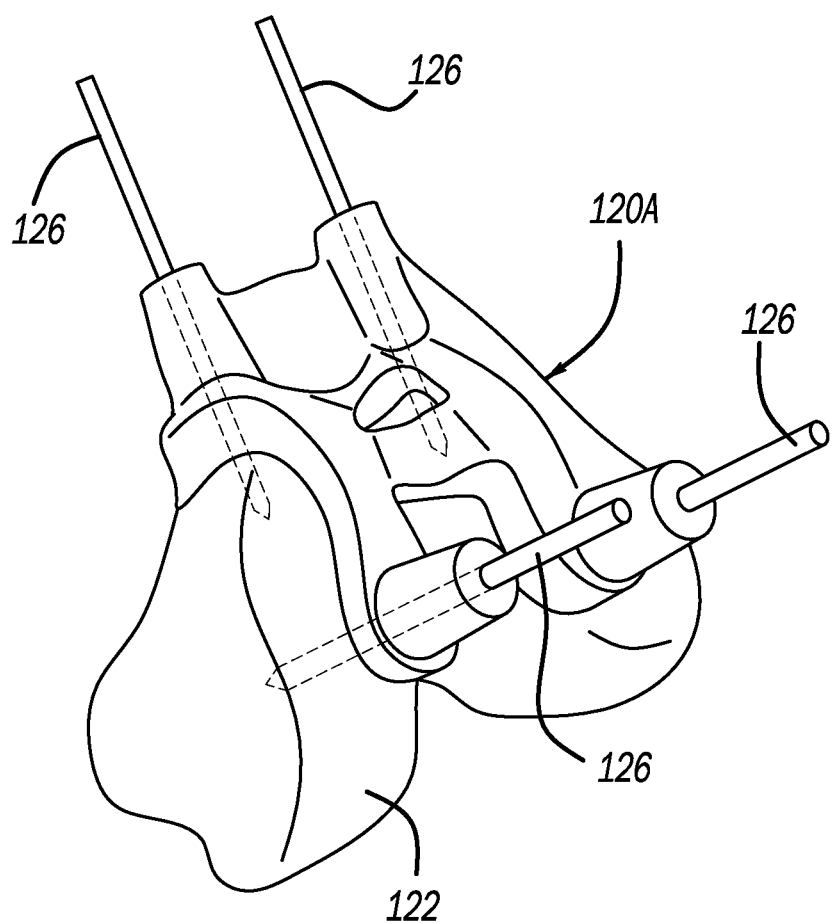
FIG. 8A is an anterior/lateral view of a femur having a patient specific guide fixed thereto according to one prior art example.
Figure 8B:
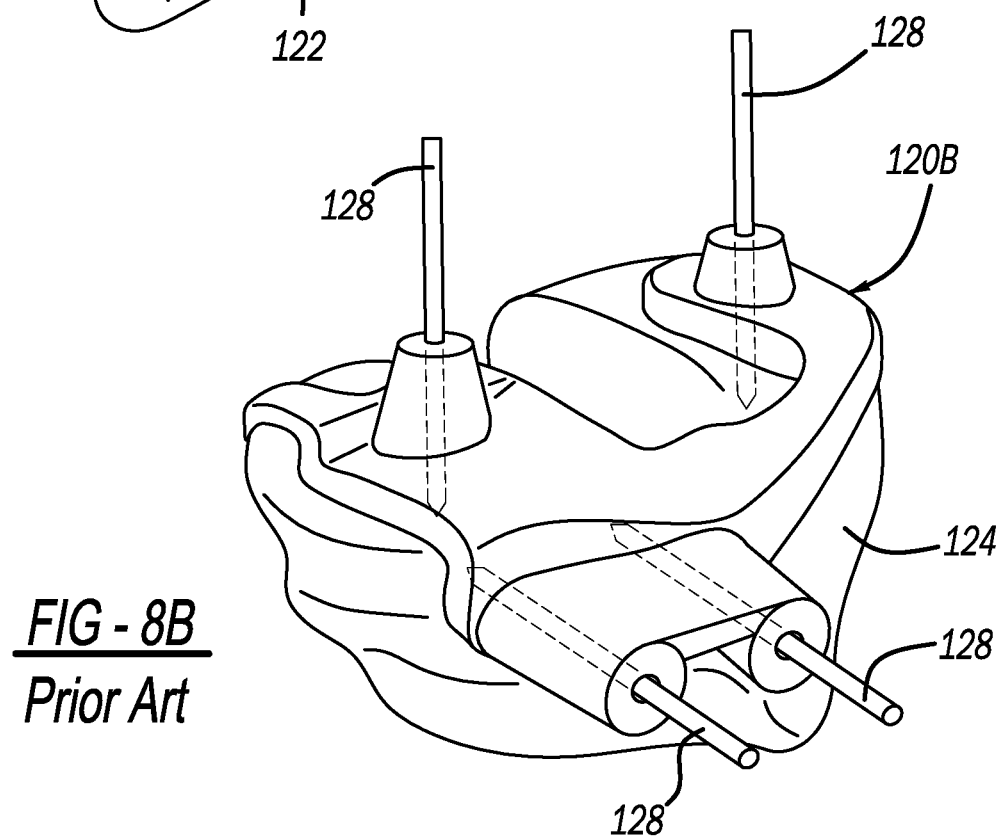
FIG. 8B is an anterior/lateral view of a tibia having a patient specific guide fixed thereto according to one prior art example.

With reference now to FIGS. 8A-11, the present teachings will be described in the context of knee replacement surgery. FIGS. 8A and 8B shows a prior art example of a patient specific guide (see femoral guide 120A and tibial guide 120B) for knee replacement surgery. The femoral guide 120A can be fixed to the femur 122 by pins 126. Similarly, the tibial guide 120B cab be fixed to the tibia 124 by pins 128. Various cut guides (not specifically shown) can then be coupled to the pins 126, 128 for directing cuts into the respective femur 122 and tibia 124.

Figure 9A:
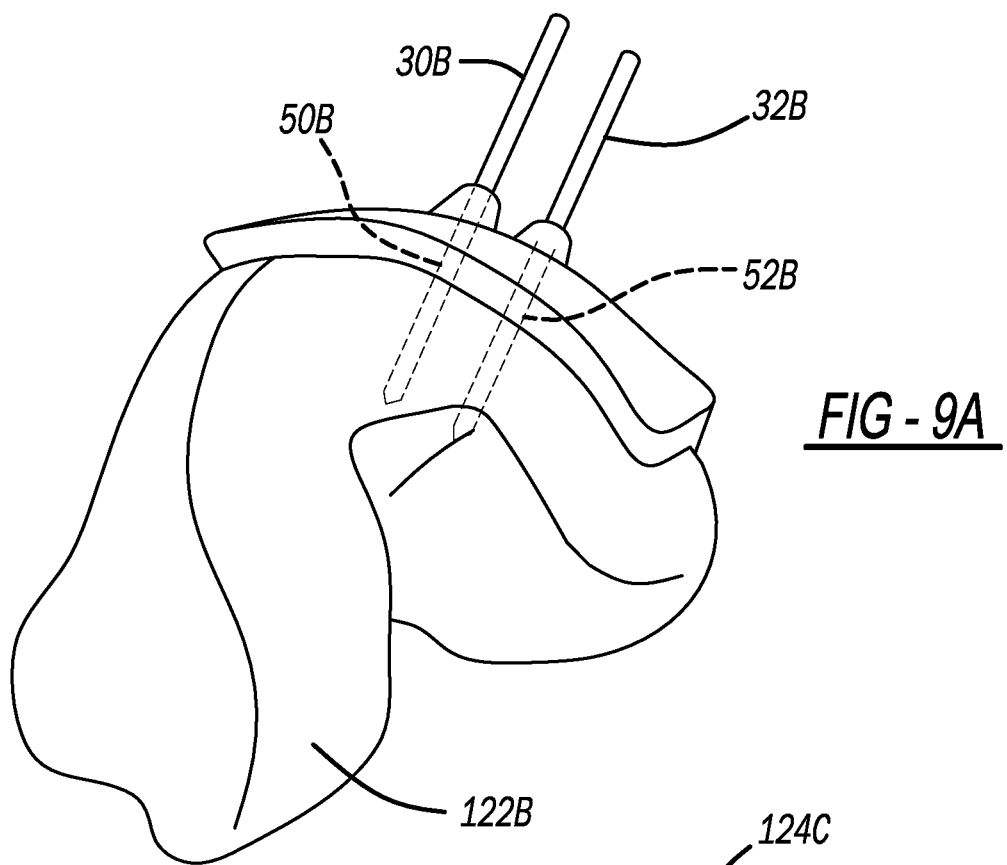
FIG. 9A is an anterior/lateral view of a femur showing a patient specific femoral guide constructed in accordance to the present disclosure coupled thereto and further shown with a pair of pins directed into the femur by the patient specific femoral guide at locations determined by a preoperative plan.
Figure 9B:
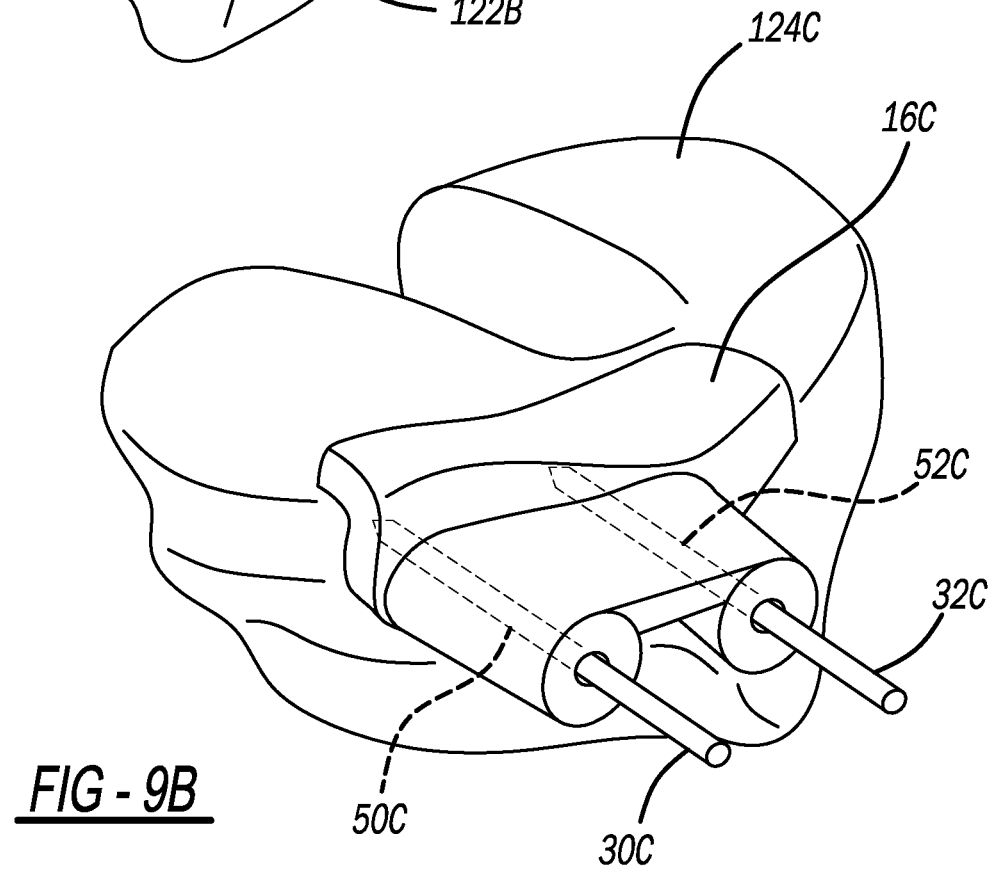
FIG. 9B is an anterior/lateral view of a tibia having a patient specific tibial guide constructed in accordance to the present disclosure coupled thereto and further shown with a pair of pins directed into the tibia by the patient specific tibial guide at locations determined by a preoperative plan.
Figure 10:
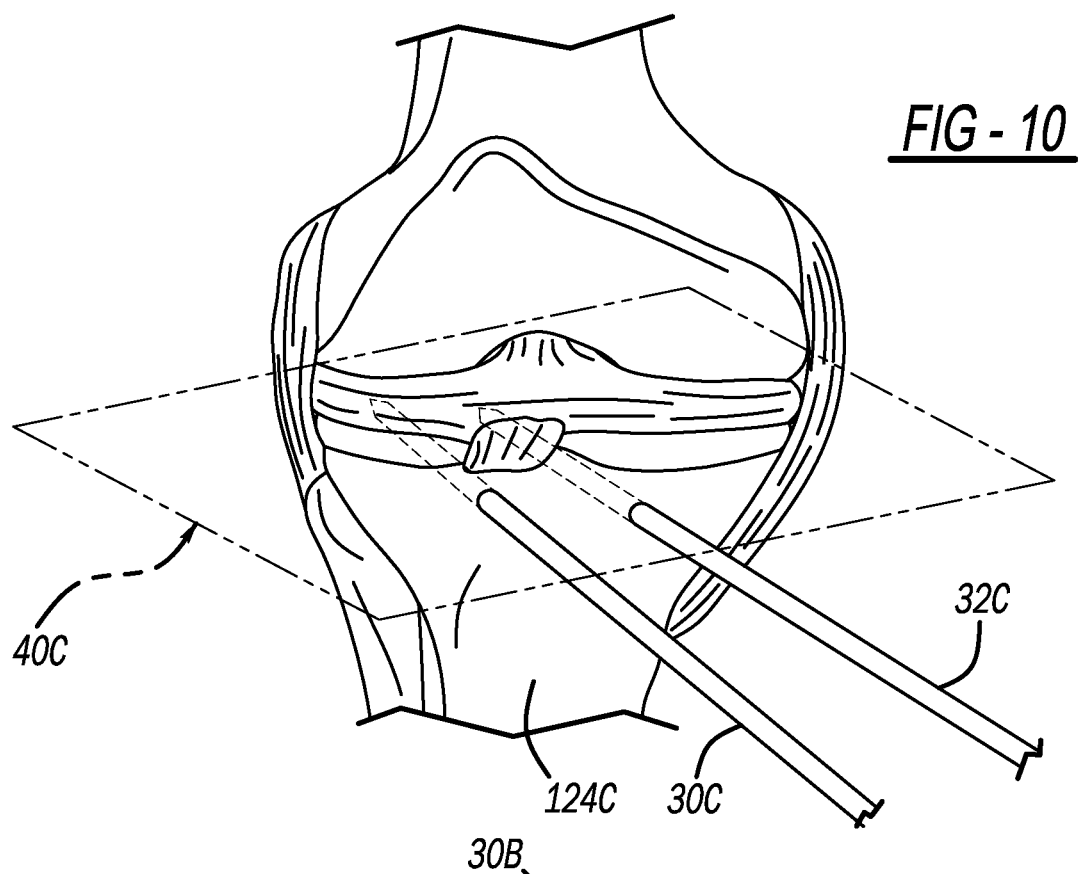
FIG. 10 is an anterior view of a right knee showing first and second pins located into an anterior tibia using the patient specific tibial guide of FIG. 9B for establishing an Alpha plane that is referenced while carrying out a preoperative plan for preparing the tibia for receipt of a tibia component.
Figure 11:
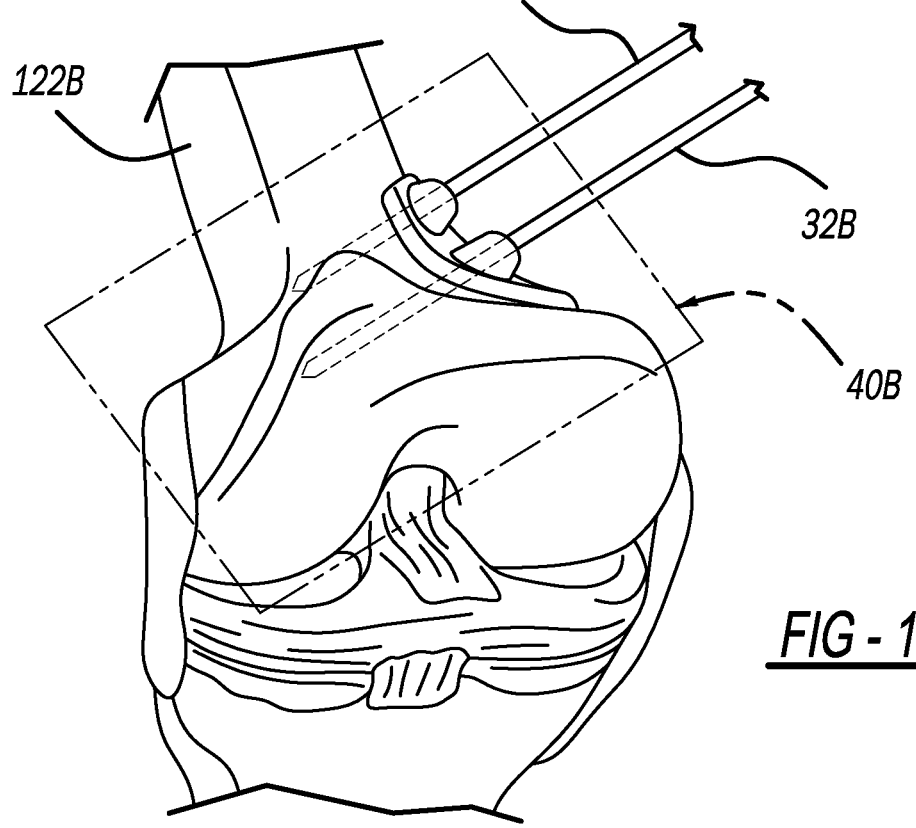
FIG. 11 is an anterior/lateral view of a right knee showing first and second pins located into a medial femur using the patient specific femoral guide of FIG. 9A.

FIGS. 9A and 9B shows patient specific femoral guide 16B and tibial guide 16C created using methods according to the present disclosure. It will be appreciated that the geometry of the patient specific femoral and tibial guides 16B and 16C is merely exemplary and that the guides 16B and 16C may take other shapes. The system 8 creates a preoperative plan 14 as described above with respect to shoulder surgery much the same way for knee surgery. The system 8 designs a patient specific femoral guide 16B and a patient specific tibial guide 16C. The guides can be manufactured based on the designs created by the system 8. The patient specific femoral guide 16B defines two cannulations or parallel bores 50B, 52B that will receive and allow placement of two parallel pins 30B, 32B. The pins 30B, 32B are used to define an Alpha plane 40B that will subsequently serve as a reference to the patients' femur 122B. The patient specific tibial guide 16C defines two cannulations or parallel bores 50C, 52C that will receive and allow placement of two parallel pins 30C, 32C. The pins 30C, 32C are used to define an Alpha plane 40C that will subsequently serve as a reference to the patients' tibia 124C.

The pins 30B and 32B will then serve to define the Alpha plane 40B. Similarly, the pins 30C and 32C will serve to define the Alpha plane 40C. As described above, the pins 30B, 32B (and 30C, 32C) can be referenced directly or indirectly during future surgical bone preparation by the surgical cutting tools 24. As the location of the pins 30B, 32B and Alpha plane 40B (and pins 30C, 32C and Alpha plane 40C) is known and determined by the preoperative plan 14, no subsequent surface mapping is required. A position of a cutting tool is known relative to the Alpha plane 40B and 40C therefore, precise cuts can be carried out relative to the Alpha plane 40B and 40C while carrying out the preoperative plan 14.

Figure 12:
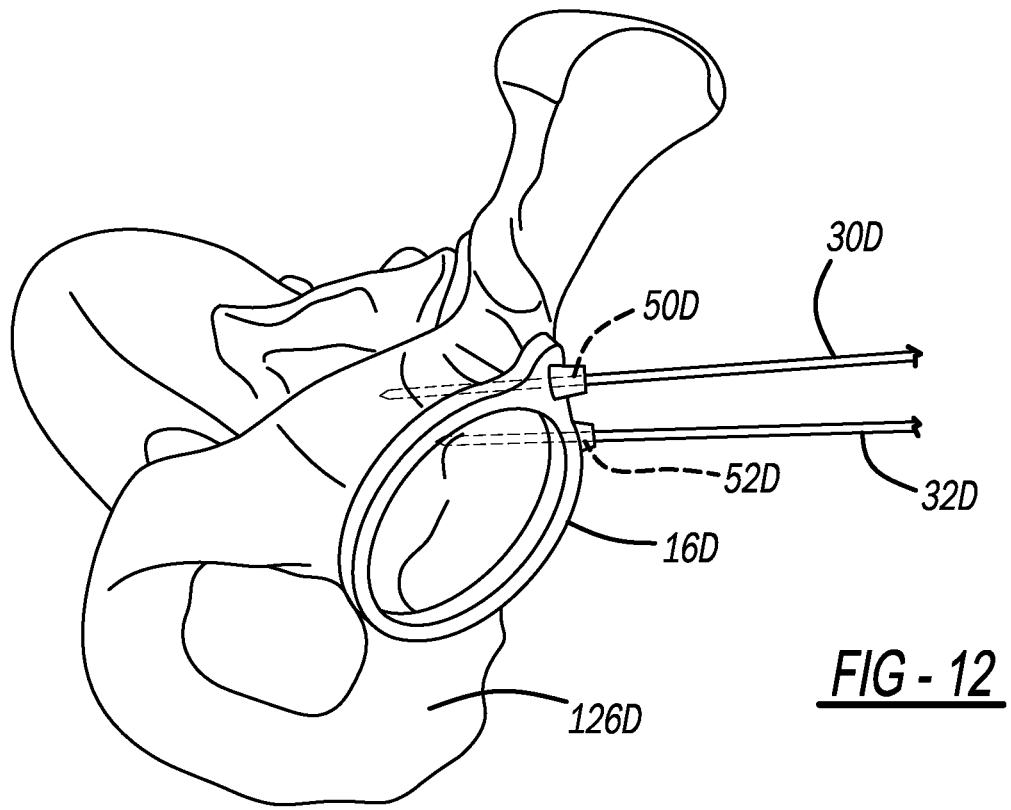
FIG. 12 is a lateral view of an acetabulum shown with a patient specific acetabular guide constructed in accordance to one example of the present disclosure coupled thereto and further shown with a pair of pins directed into the acetabulum by the patient specific acetabular guide at locations determined by a preoperative plan.
Figure 13:
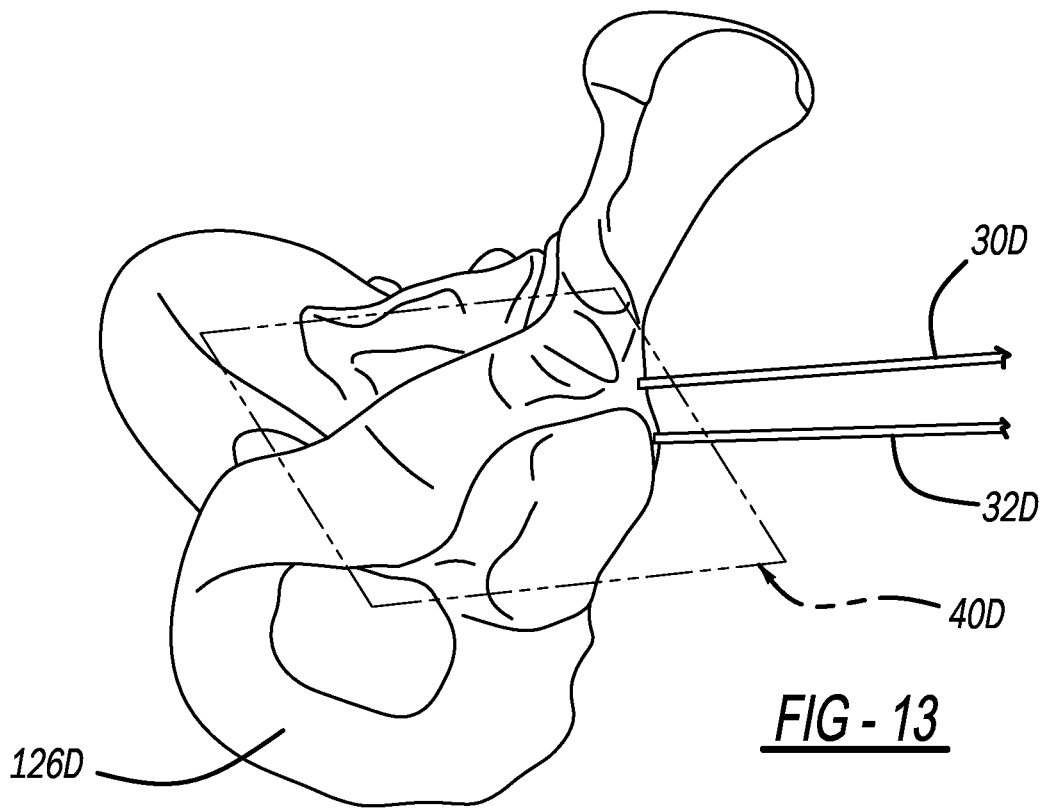
FIG. 13 is a lateral view of an acetabulum showing first and second pins located into the acetabulum using the patient specific acetabular guide of FIG. 12 for establishing an Alpha plane that is referenced while carrying out a preoperative plan for preparing the acetabulum for receipt of an acetabular component.

With reference now to FIGS. 12 and 13, the present teachings will be described in the context of hip replacement surgery. FIG. 12 shows a patient specific acetabular guide 16D created using methods according to the present disclosure. It will be appreciated that the geometry of the patient specific acetabular guide 16D is merely exemplary and that the acetabular guide 16D may take other shapes. The system 8 creates a preoperative plan 14 as described above with respect to shoulder surgery much the same way for hip surgery. The system 8 creates a patient specific acetabular guide 16D having two cannulations or parallel bores 50D, 52D that will receive and allow placement of two parallel pins 30D, 32D. The pins 30D, 32D are used to define an Alpha plane 40D that will subsequently serve as a reference to the patients' acetabulum 125D.

As described above, the pins 30D and 32D can be referenced directly or indirectly during future surgical bone preparation by the surgical cutting tools 24. As the location of the pins 30D and 32D (and Alpha plane 40D) is known and determined by the preoperative plan 14, no subsequent surface mapping is required. A position of a cutting tool is known relative to the Alpha plane 40D therefore, precise cuts can be carried out relative to the Alpha plane 40D while carrying out the preoperative plan 14.

Figure 14:
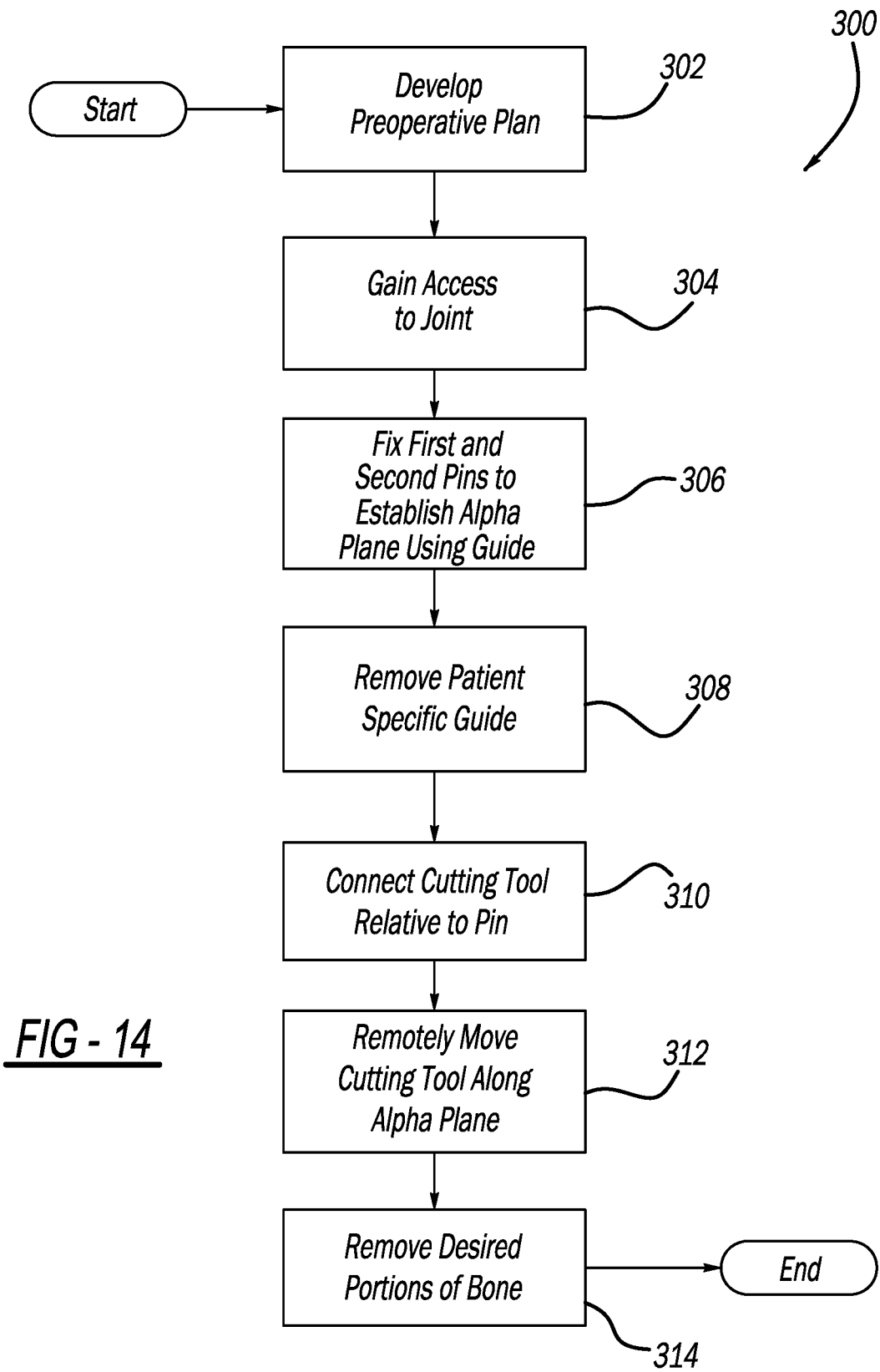
FIG. 14 is an exemplary method for performing arthroplasty of an anatomical joint for receipt of an implant according to one example of the present disclosure.

With reference now to FIG. 14, an exemplary method for performing arthroplasty of an anatomical joint for receipt of an implant according to one example of the present disclosure is shown and generally identified at reference 300. At 302 a preoperative plan is developed. The preoperative plan can establish a desired amount of remaining first bone based on the condition of the anatomical joint and a desired orientation of the implant and known parameters. The known parameters can include a valgus angle (such as between 3 degrees and 6 degrees of valgus for knee replacement), retroversion angle (such as between 0 and 10 degrees of retroversion for a glenoid component), or other parameter specific to the implant and patient anatomy. At 304 access to the anatomical joint is gained to expose the first bone and a patent specific guide is located thereat. The patient specific guide is designed to only fit onto that specific patient in one orientation. In this regard, confirmation that the patient specific guide is properly positioned is easily achieved. First and second pins are fixed into the first bone thereby establishing an Alpha plane at 306. The patient specific guide is removed at 308. A cutting tool is connected to at least one of the first and second pins at 310. The cutting tool is remotely moved relative to one of the first and second pins along the Alpha plane at 312. The desired portions of the first bone are removed with the cutting tool while referencing the Alpha plane exclusively based on the preoperative plan at 314. Again, as mentioned above, the exemplary method of FIG. 14 and related system can be adapted to any anatomical bone such as bones included in the shoulder, knee and hip joints.

Figure 15:
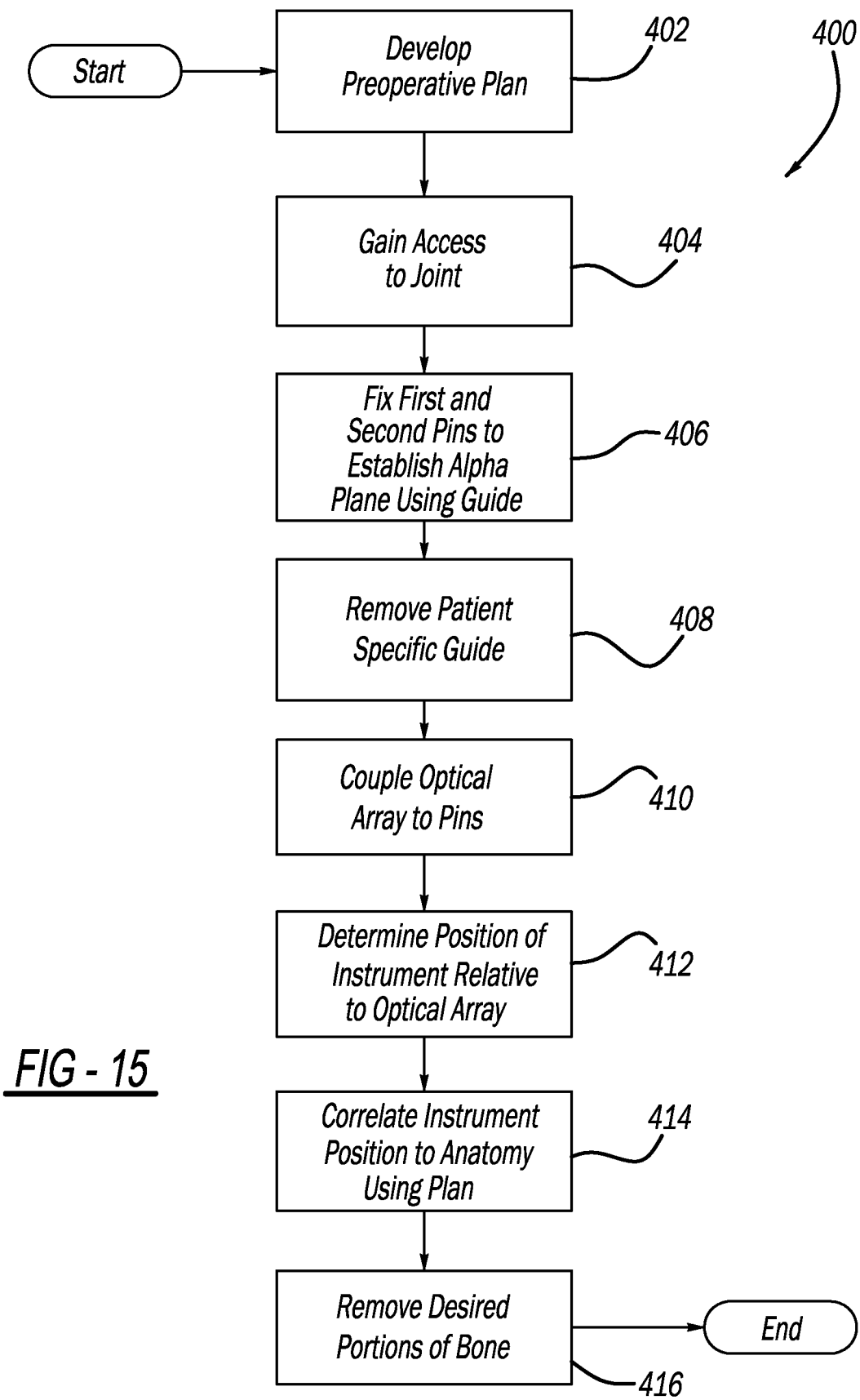
FIG. 15 is an exemplary method for performing arthroplasty of an anatomical joint for receipt of an implant according to another example of the present disclosure.

With reference now to FIG. 15, an exemplary method for performing arthroplasty of an anatomical joint for receipt of an implant according to another example of the present disclosure is shown and generally identified at reference 400. At 402 a preoperative plan is developed. The preoperative plan can establish a desired bone cutting depth of a first bone and a desired amount of remaining first bone based on the condition of the anatomical joint. At 404 access to the anatomical joint is gained to expose the first bone and a patent specific guide is located thereat. First and second pins are fixed into the first bone thereby establishing an Alpha plane at 406. The patient specific guide is removed at 408. Optical arrays are coupled to the pins at 410. The position of a surgical instrument or tool relative to the optical arrays is determined at 412. The distance between the bone and where on the pins the arrays are coupled must be defined. In this regard, the optical arrays will be clipped or otherwise fixed to the pins at a defined distance from the bone. The instrument position is correlated to the patients' anatomy using the preoperative plan at 414. The desired portions of the first bone are removed with the cutting tool while referencing the Alpha plane exclusively based on the preoperative plan at 316. Again, as mentioned above, the exemplary method of FIG. 15 and related system can be adapted to any anatomical bone such as bones included in the shoulder, knee and hip joints.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known procedures, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

As used herein, the term module may refer to, be part of, or include: an Application Specific Integrated Circuit (ASIC); an electronic circuit; a combinational logic circuit; a field programmable gate array (FPGA); a processor or a distributed network of processors (shared, dedicated, or grouped) and storage in networked clusters or datacenters that executes code or a process; other suitable components that provide the described functionality; or a combination of some or all of the above, such as in a system-on-chip. The term module may also include memory (shared, dedicated, or grouped) that stores code executed by the one or more processors.

The term code, as used above, may include software, firmware, byte-code and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

What is claimed is:

1. A method of performing arthroplasty of an anatomical joint for receipt of an implant, the method comprising:
   developing a preoperative plan that includes establishing a desired amount of remaining first bone;
   designing a patient specific guide based on the preoperative plan, the patient specific guide having a pair of bores defined therein located in positions to accept a complementary pair of rigid pins at locations on the patient specific guide to orient the respective pins in a direction optimized for surgeon access to the first bone and to establish an Alpha plane, the preoperative plan including known locations of the first bone relative to the Alpha plane;
   placing the patient specific guide relative to the first bone;
   advancing the pair of pins through the pair of bores on the patient specific guide;
   fixing the pair of pins into the first bone thereby establishing the Alpha plane;
   removing the patient specific guide from the first bone wherein the first bone is therefore only engaged by the pair of pins; and
   removing bone according to the preoperative plan while referencing exclusively the Alpha plane.

2. The method of claim 1 wherein executing the preoperative plan comprises:
   coupling optical arrays to the pair of pins at a known distance from the first bone;

correlating a position of a cutting tool relative to the Alpha plane using the optical arrays; and removing desired portions of the first bone with the cutting tool while referencing exclusively the Alpha plane to determine a position of the cutting tool based on the preoperative plan.

3. The method of claim 1 wherein executing the preoperative plan comprises:

connecting a cutting tool relative to at least one of the first and second pins;

moving the cutting tool relative to at least one of the first and second pins and along the Alpha plane;

removing desired portions of the first bone with the cutting tool while referencing exclusively the Alpha plane to determine a position of the cutting tool based on the preoperative plan.

4. The method of claim 3 wherein connecting the cutting tool comprises:

clamping a portion of the cutting tool to the at least one pin for translation of the cutting tool along the at least one pin.

5. The method of claim 4 wherein removing the desired portions of the first bone comprises:

translating the cutting tool along the Alpha plane;

reaming first portions of the first bone with the cutting tool at a first cutting angle based on the preoperative plan;

articulating an arm on the cutting tool to establish a second cutting angle, distinct from the first angle;

further translating the cutting tool along the Alpha plane; and reaming second portions of the first bone with the cutting tool at the second cutting angle based on the preoperative plan.

6. The method of claim 1 wherein removing desired portions of the first bone comprises:

resecting the first bone in a pattern to match a geometry of an implant.

7. The method of claim 1 wherein the cutting tool is motorized.

8. The method of claim 7 wherein the cutting tool communicates wirelessly with a computer having the preoperative plan.

9. The method of claim 8 wherein the computer comprises one of a workstation, desktop, laptop, tablet, mobile phone, wearable accessory or garment.

10. The method of claim 7 wherein the cutting tool comprises one of a reamer and an end-cutting milling device.

11. The method of claim 1 wherein the first bone is a glenoid and the anatomical joint is a shoulder, wherein the first pin is fixed into a base of a coracoid.

12. The method of claim 1 wherein the first bone is a femur and the implant is a femoral implant.

13. The method of claim 1 wherein the first bone is a tibia and the implant is a tibia implant.

14. The method of claim 1 wherein the first bone is an acetabulum and the implant is an acetabular cup.

15. A method of performing arthroplasty of a shoulder for receipt of an implant, the method comprising:

developing a preoperative plan that includes establishing a desired amount of remaining glenoid based on a condition of the shoulder and a desired orientation of the implant;

designing a patient specific guide based on the preoperative plan, the patient specific guide having a pair of bores defined therein located in positions to accept a complementary pair of rigid pins whereby the bores are arranged at locations on the patient specific guide to orient the respective pins in a direction optimized for surgeon access to the glenoid and to establish an Alpha plane, the preoperative plan including known locations of the glenoid relative to the Alpha plane;

placing the patient specific guide relative to the glenoid;

fixing the pair of pins relative to the patient specific guide into a coracoid of the glenoid thereby establishing the Alpha plane;

removing the patient specific guide from the glenoid; and locating a portion of a cutting tool relative to the at least one pin and moving the cutting tool relative to the at least one pin to remove bone while referencing the Alpha plane thereby executing the preoperative plan.

16. The method of claim 15 wherein executing the preoperative plan comprises:

coupling optical arrays to the pair of pins at a known distance from the glenoid;

correlating a position of a cutting tool relative to the Alpha plane using the optical arrays; and removing desired portions of the glenoid with the cutting tool while referencing exclusively the Alpha plane to determine a position of the cutting tool based on the preoperative plan.

17. A method of performing arthroplasty of a hip for receipt of an acetabular cup, the method comprising:

developing a preoperative plan that includes establishing a desired amount of remaining acetabulum based on a condition of the hip and a desired orientation of the acetabular cup;

designing a patient specific guide based on the preoperative plan, the patient specific guide having a pair of bores defined therein located in positions to accept a complementary pair of rigid pins whereby the bores are arranged at locations on the patient specific guide to orient the respective pins in a direction optimized for surgeon access to the acetabulum and to establish an Alpha plane, the preoperative plan including known locations of the acetabulum relative to the Alpha plane;

placing the patient specific guide relative to the acetabulum;

fixing the pair of pins relative to the patient specific guide into the acetabulum thereby establishing the Alpha plane;

removing the patient specific guide from the acetabulum; and locating a portion of a cutting tool relative to the at least one pin and moving the cutting tool relative to the at least one pin to remove bone while referencing the Alpha plane thereby executing the preoperative plan.

18. The method of claim 17 wherein executing the preoperative plan comprises:

coupling optical arrays to the pair of pins at a known distance from the acetabulum;

correlating a position of a cutting tool relative to the Alpha plane using the optical arrays; and removing desired portions of the acetabulum with the cutting tool while referencing exclusively the Alpha plane to determine a position of the cutting tool based on the preoperative plan.

\* \* \* \* \*